(12) United States Patent
Brambrink et al.

(10) Patent No.: US 10,285,580 B2
(45) Date of Patent: May 14, 2019

(54) VIDEO ENDOSCOPE

(71) Applicants: Karl Storz SE & Co. KG, Tuttlingen (DE); Oregon Health & Sciende University, Portland, OR (US)

(72) Inventors: Ansgar Brambrink, Portland, OR (US); Thomas Ruegg, Schaffhausen (CH); Dieter Huels, Stockach (DE); Christian Huber, Schaffhausen (CH); Andreas Efinger, Tuttlingen (DE); Martin Renner, Tuttlingen (DE)

(73) Assignees: Karl Storz SE & Co. KG, Tuttlingen (DE); Oregon Health & Science University, Portland, OR (US)

( * ) Notice: Subject to any disclaimer, the term of this patent is extended or adjusted under 35 U.S.C. 154(b) by 176 days.

(21) Appl. No.: 15/142,081

(22) Filed: Apr. 29, 2016

(65) Prior Publication Data
US 2016/0317009 A1 Nov. 3, 2016

(30) Foreign Application Priority Data
Apr. 29, 2015 (DE) .................... 10 2015 106 609

(51) Int. Cl.
*A61B 1/01* (2006.01)
*A61B 1/00* (2006.01)
(Continued)

(52) U.S. Cl.
CPC .......... *A61B 1/267* (2013.01); *A61B 1/00018* (2013.01); *A61B 1/0052* (2013.01);
(Continued)

(58) Field of Classification Search
CPC . A61B 1/00066; A61B 1/00128; A61B 1/005; A61B 1/0052; A61B 1/0057
(Continued)

(56) References Cited

U.S. PATENT DOCUMENTS 4,589,403 A * 5/1986 Ouchi .................... A61B 1/126
600/104
4,986,257 A * 1/1991 Chikama .............. A61B 1/0052
600/146
(Continued)

FOREIGN PATENT DOCUMENTS

| DE | 10100533 A1 | 7/2002 |
| EP | 2072001 A2 | 6/2009 |
| WO | 2014127780 A1 | 8/2014 |

OTHER PUBLICATIONS

Extended European Search Report Application No. EP 16167268.8 Completed: Jul. 13, 2016; dated Jul. 22, 2016 8 pages.
(Continued)

*Primary Examiner* — Timothy J Neal
*Assistant Examiner* — Jae Woo
(74) *Attorney, Agent, or Firm* — Whitmyer IP Group LLC (57) ABSTRACT

A video endoscope comprises a shaft comprising a rigid, proximal-side section and a distal section that is laterally deflectable in a plane from the central longitudinal axis of the shaft. A housing is arranged at the proximal end of the shaft. A control element for controlling the deflection of the shaft is provided at the housing. A rod-like pull element extends in the shaft in an off-center fashion with respect to the central longitudinal axis. The pull element is coupled with the control element and with a distal end of the deflectable section of the shaft, wherein a movement of the pull element by the control element in the proximal direction effects a lateral deflection of the deflectable section. A push tube is provided that is arranged to encase the exterior side of the pull element. The push tube extends from the proximal connection of the pull element with the control element through the first opening into the shaft.

20 Claims, 5 Drawing Sheets

(51) Int. Cl.
  *A61B 1/267* (2006.01)
  *A61B 1/005* (2006.01)
  *A61B 1/05* (2006.01)
  *A61B 1/06* (2006.01)
  *A61M 16/04* (2006.01)

(52) U.S. Cl.
  CPC .......... *A61B 1/0056* (2013.01); *A61B 1/0057* (2013.01); *A61B 1/00114* (2013.01); *A61B 1/00154* (2013.01); *A61B 1/01* (2013.01); *A61B 1/05* (2013.01); *A61B 1/0676* (2013.01); *A61B 1/0684* (2013.01); *A61M 16/0488* (2013.01)

(58) Field of Classification Search
  USPC ................................ 600/146, 120, 130, 139
  See application file for complete search history.

(56) References Cited

U.S. PATENT DOCUMENTS

| | | | | |
|---|---|---|---|---|
| 5,097,838 A * | 3/1992 | Hirooka | ............. | A61B 1/00098 600/463 |
| 5,168,864 A * | 12/1992 | Shockey | ............. | A61B 1/0056 600/131 |
| 5,299,562 A * | 4/1994 | Heckele | ............. | G02B 23/2423 600/140 |
| 5,460,168 A * | 10/1995 | Masubuchi | ........ | A61B 1/00096 600/107 |
| 5,916,146 A * | 6/1999 | Allotta | ................ | A61B 1/0051 600/139 |
| 6,117,071 A * | 9/2000 | Ito | ..................... | A61B 1/00059 600/118 |
| 6,319,195 B1 * | 11/2001 | Nakaichi | ............. | A61B 1/0052 600/120 |
| 6,319,315 B1 | 11/2001 | Sanjoh | | |
| 6,699,182 B2 | 3/2004 | Pilvisto | | |
| 8,133,170 B2 * | 3/2012 | Miyawaki | .......... | A61B 1/00078 600/139 |
| 8,998,801 B2 | 4/2015 | Okazaki | | |
| 9,066,656 B2 * | 6/2015 | Irion | ................... | A61B 1/00071 |
| 2003/0069475 A1 * | 4/2003 | Banik | ................ | A61B 1/00016 600/152 |
| 2006/0270975 A1 * | 11/2006 | Savage | ............. | A61M 25/0054 604/95.04 |
| 2006/0270976 A1 * | 11/2006 | Savage | ............. | A61B 17/2202 604/95.04 |
| 2008/0188868 A1 * | 8/2008 | Weitzner | .............. | A61B 1/0014 606/130 |
| 2010/0191053 A1 * | 7/2010 | Garcia | ............... | A61B 1/00105 600/109 |
| 2011/0288375 A1 * | 11/2011 | Ouchi | .................. | A61B 1/0052 600/114 |
| 2012/0041264 A1 * | 2/2012 | Blase | ................. | A61B 1/00078 600/121 |
| 2014/0066715 A1 * | 3/2014 | Nagaoka | ........... | A61B 1/00057 600/127 |
| 2015/0351609 A1 * | 12/2015 | Fan | ...................... | A61B 1/0052 600/109 |
| 2015/0366436 A1 * | 12/2015 | Iuel | ..................... | A61B 1/0052 600/149 |
| 2016/0228113 A1 * | 8/2016 | Weitzner | .............. | A61B 1/0014 |

OTHER PUBLICATIONS

German Search Report Application No. 10 2015 106 609.2 dated Mar. 9, 2016 12 pages.

* cited by examiner

VIDEO ENDOSCOPE

CROSS-REFERENCES TO RELATED APPLICATIONS

This application claims priority from German patent application 10 2015 106 609.2, filed on Apr. 29, 2015. The entire content of that priority application is fully incorporated by reference herewith.

BACKGROUND

The present disclosure generally relates to the field of endoscopes and video endoscopes. More particularly, the present disclosure relates to endoscopes that are arranged to be used in the field of intubation, such as video intubation endoscopes.

More particularly, in one exemplary aspect, the present disclosure relates to a video endoscope, the endoscope comprising a shaft comprising a rigid, proximal-side section and a distal section that is laterally deflectable in a plane from the central longitudinal axis of the shaft, wherein an imager and an illuminator are arranged at the distal end of the deflectable section, and wherein a housing is arranged at the proximal end of the shaft, wherein the housing comprises a control element for controlling the deflection of the shaft, wherein a rod-like pull element extends in the shaft in a fashion off-center with respect to the central longitudinal axis, wherein the pull element is, at the proximal side thereof, coupled with the control element and, at a distal side thereof, coupled with the distal end region of the deflectable distal section of the shaft, wherein a movement of the pull element by the control element in the proximal direction effects a lateral deflection of the deflectable section, wherein the rod-like pull element extends into a clearance space in the interior of the housing through a first opening at the proximal end of the shaft, wherein the proximal end of the pull element is coupled with the control element in the clearance space.

An intubation endoscope of that kind is known from U.S. Pat. No. 6,319,195 B1.

For intubation, particularly for emergency intubation, instruments are required by which means for ventilating the patient may be inserted in the trachea as quickly as possible. Emergency situations of that kind particularly occur after accidents in which the trachea and, as a consequence, the respiration of the patient is strongly restricted or entirely blocked. In particular, emergency situations of that kind occur in connection with work accidents, road accidents and particularly motor cycle accidents. For such an emergency intubation, an instrument needs to be provided which is preferably operable in a simple and reliable fashion.

To this end, intubation endoscopes have been developed. In some exemplary embodiments, an intubation tube is made from transparent plastic material may be placed on the distal end region of such an intubation endoscope, wherein the intubation tube may be inserted into the trachea with that intubation endoscope, involving visual observation. Having inserted the intubation tube, the intubation tube in inflated so that the intubation tube is arranged to remain fixed on location in the trachea. Subsequently, the intubation endoscope is pulled off from the inserted tube. Thereafter, the tube is coupled with a hose of a ventilation apparatus by means of which ventilation air subsequently may be supplied to the trachea.

In such intubation cases, often minutes or even seconds determine whether the patient may be ventilated again in time such that the survival of the patient may be ensured.

Further, there is a desire to provide the shaft of the intubation endoscope with a diameter as small as possible so that a correspondingly greater and more stable intubation tube may be attached thereon and inserted into the trachea. As the anatomical structure for the intubation of human patients are widely similar, an endoscope is used which comprises a rigid straight shaft region, the distal end region of which is laterally deflectable. Due to the anatomy of humans, an endoscope having a distal deflection in only one direction is sufficient. It is more favorable, in terms of ergonomics, to use such an endoscope that is merely deflectable in a single direction than using systems providing a deflection in two or potentially four directions. The intubation endoscope is initially, having a straight orientation, inserted in the oral cavity towards the larynx and, thereafter, the deflectable section is curved in a manner that corresponds to the transition of the oral cavity via the larynx to the trachea of the respective patient.

A further requirement is that the endoscopic visualization system is preferably small in diameter so as to provide a sufficient cross-sectional surface for the intubation tube for ventilation. In accordance with the afore-mentioned U.S. Pat. No. 6,319,195 B1, a correspondingly slender elongated shaft is formed the distal end region of which is laterally deflectable in one direction. To this end, a basically rod-like pull element is arranged in the interior in a fashion offset from the central longitudinal axis of the shaft, wherein the distal end of the pull element is coupled with the deflectable region. The proximal end of the pull element is fed through an opening into an inner clearance space of a housing which is arranged at a proximal-side end of the shaft. At the housing, a laterally projecting control element that forms a control lever is provided, the inner end of which extends in the interior space, namely in the clearance space, and is coupled therein with the proximal end of the pull element. In the linearly straightened state of the shaft, the lever laterally projects from the housing. When the lever approaches the housing, the proximal end of the pull element is pulled in the proximal direction into the inner clearance space of the housing. This consequently involves that the flexible section of the shaft is laterally deflected.

The resetting of the deflected shaft to the rectilinear state is performed by a rebound element arranged in the interior of the shaft, wherein the rebound element is arranged as an elastic element that is coupled with the distal end region of the pull element. When laterally deflecting the shaft, a reset force is generated in the rebound element which provides for the rectilinear orientation of the shaft when the lever is released.

Depending on the configuration of the imaging and illumination system by which processes at the distal end of the shaft may be visually acquired during the intubation, also respective supply lines must be fed through the shaft, that is, light conductors, image conductors or corresponding electrical supply lines.

As the pull element is, in practical use, subjected to tension, that is, displaced in the proximal direction, the pull element may be configured to have a relatively small diameter, for instance as a slender wire body by which considerable pull forces may be applied.

When deflecting the shaft, the proximal end region of the pull element which is coupled with the control element is moved by a certain distance into the clearance space in the interior of the housing.

It has been observed with pull elements having a relatively small diameter, in practical use, that bulges or lateral deflections of the pull element may occur when aligning the shaft in a rectilinear fashion, when the portion of the pull element that is arranged in an exposed fashion in the interior is moved in the distal direction.

These bulges involve that a movement of the pull element in the distal direction for straightening the shaft or for reducing the curvature of the deflected region when adapting to the respective anatomy of the patient may be inhibited or blocked by such bulges or deflections.

In view of this it is an object of the present disclosure to address and tackle at least some of the above-mentioned drawbacks and issues.

It is another object to provide a remedy for at least some of the above-mentioned drawbacks and to present an endoscope that may be operated in an ergonomic and reliable fashion.

It is a further object to present an endoscope that also may be operated as an intubation endoscope, and wherein the back-and-forth motion of the pull element, particularly the displacement in the distal direction, is performed in a reliable fashion.

SUMMARY

These and other objects of the present disclosure are achieved by a video endoscope, comprising a shaft comprising a rigid, proximal-side section, and a distal section that is laterally deflectable from a central longitudinal axis of the shaft, an imager and an illuminator that are arranged at a distal end of the deflectable section, a rod-like pull element arranged in the shaft in an off-center fashion with respect to the central longitudinal axis, a housing that is arranged at a proximal end of the shaft, a control element arranged at the housing for controlling the deflection of the shaft, and a push tube that encases an exterior side of the pull element, wherein the pull element is, at a proximal side thereof, coupled with the control element and, at a distal side thereof, coupled with the distal end of the deflectable section of the shaft in such a way that a movement of the pull element in the proximal direction that is induced by the control element effects a lateral deflection of the deflectable section, wherein the rod-like pull element extends into an interior clearance of the housing through a first opening at the proximal end of the shaft, wherein a proximal end of the pull element is coupled with the control element in the clearance space, forming a proximal connection, wherein the push tube extends from the proximal connection of the pull element with the control element through the first opening into the shaft, when the shaft is straightened, and wherein the push tube is arranged to fully cover a region of the pull element that is arranged in the clearance space of the interior of the housing when the pull element is maximally displaced in the proximal direction.

In accordance with an exemplary embodiment of an endoscope as mentioned in the outset, a push tube encases the exterior side of the pull element which extends from the proximal connection of the pull element with the control element through the first opening into the shaft, when the shaft is straightened, wherein the length of the push tube is defined in such a way that the entire section of the pull element that is arranged in the clearance space of the housing is covered by the push tube when the pull element is maximally moved in the proximal direction.

The push tube surrounds the pull element in the section in the clearance space of the interior of the housing that is prone to lateral bulges and, in this way, prevents a lateral evasion or bulging of the pull element during the movement thereof in the distal direction into the shaft. At the pull element itself, no design modifications are necessary. In particular, it is not required to enlarge the diameter or to reinforce the material thereof. Rather, in the critical region in the interior of the housing, wherein sufficient space is provided, the push tube is provided at the exterior side of the pull element. The assembly of the pull element and the push tube encasing the exterior side thereof then comprises overall such a level of rigidity that also jerky movements of the pull element in the distal direction may be performed without lateral deflection movements or bulges.

As a result, the operational safety and also the operability of the intubation endoscope may be considerably increased without the need of taking strengthening measures in the interior of the shaft, where little installation space is provided.

In an exemplary embodiment, the proximal end of the push tube and the pull element are fixedly coupled with the control element.

Accordingly, his may be not only achieved in a technically simple fashion but that this fixed connection with the control element ensures that no relative movements in the longitudinal direction between the pull element and the encasing push tube occur. This also contributes to the operational safety.

In a further exemplary embodiment, the proximal end of the push tube, seen from proximal to distal, ends before the proximal end of the deflectable section of the shaft when the shaft is straightened.

Accordingly, freedom of design in the region of the deflectable section is not considerably influenced by the push tube. The push tube, however, is utilized for increasing the rigidity of the pull element in regard of the bulging or curving, but only in the region of the clearance space in the housing. In the region of the deflectable section, the pull element must be able to curve, as this pull element, when moved in the proximal direction, effects the curving of the deflectable section. The push tube ends before the deflectable section, as a result of that it does not influence the function, the design measures and the operational safety of the deflection.

In a further exemplary embodiment, the length of the push tube is arranged in such a way that, when the pull element is maximally moved in the proximal direction, the push tube still extends through the first opening into the shaft.

This measure further contributes to the operational safety, namely for the purpose of a proper guiding of the assembly of pull element and push tube through the opening into the shaft.

In a further exemplary embodiment, the push tube is arranged to be guided in a guide in the rigid proximal section.

This measure further enhances the before-mentioned effect, i.e. that the push tube including the pull element received therein is guided in the rigid proximal section of the shaft in a safe operation fashion.

In a further exemplary embodiment, a guide tube of the guide extends from the proximal end of the first opening into the clearance space, wherein the assembly of push tube and pull element extends through the guide tube.

This measure even further contributes to the guiding of the assembly of push tube and pull element in a safe operation fashion in such way that also a guiding in a certain region in the clearance space is present which is provided for such guiding measures.

In a further exemplary embodiment, the length of the guide tube that extends into the clearance space is defined in such a way that nearly the entire section of the assembly of pull element and push tube between the first opening and the connection with the control element is covered by the guide tube when the shaft is straightened.

This measure ensures that, when the shaft is linearly aligned, involving that the control element is maximally moved in the distal direction, the region between the connection of the assembly with the distal end of the control element and the opening through which that assembly extends into the shaft is nearly along its overall length covered by the guide tube. This measure significantly contributes to the operational safety.

In a further exemplary embodiment, the push tube is made from metal material.

This measure has the effect that already with very thin metal tubes, for instance made from stainless steel, a sufficient strengthening of the pull element against lateral deflection movements or bulges is provided so that the same may be prevented.

The material selection and the diameter of the pull element and the wall thickness of the push tube are adapted to one another in such a way that the pull element, having a design involving a diameter as small as possible, may apply the required pull forces for deflecting the shaft in a reliable fashion and that the push tube may prevent a lateral evasion of the pull element in the clearance space when linearly aligning the shaft.

This exemplary set-up measure has the effect that, when designing such an intubation endoscope, the diameter of the pull element possibly may be further reduced so that extremely thin shafts may be manufactured. As indicated above, it is a goal to apply preferably large and stable intubation tubes. The diameter of the pull element in the shaft may be defined to be so small that just sufficient pull forces may be transferred in a reliable fashion so as to effect a deflection of the shaft. The critical exposed region in the interior clearance space of the push tube may be now utilized to push respective rigid or stable push tubes over the proximal end region of the pull element which is pulled in the proximal direction into the housing and therefore exposed when the shaft is deflected. In other words, in accordance with at least some embodiments as discussed herein, there is provided the opportunity to implement even more slender shafts with more slender pull elements.

In a further exemplary embodiment, a supply cable extends through the shaft which is, at a distal side thereof, coupled with the imager and the illuminator that are arranged as a unit and which extends through a second opening at the proximal end of the shaft into the clearance space.

In the context of the miniaturization of illuminators and imagers, it is now enabled to arrange a Video-/LED-unit having an extremely small diameter at the distal end of the shaft, wherein the unit provides a brilliant image when a sufficient illumination is present. This supply cable that is required to this end also must be guided through the shaft and may pass through a second opening into the clearance space of the housing without influencing the assembly of the push tube and the pull wire.

In a further exemplary embodiment, the supply cable is arranged as a flat ribbon cable and a guide channel is formed in the deflectable section being arranged, in cross-section, as an elongated hole, wherein the longer axis of the elongated hole opening extends transversely to the swivel plane of the deflectable section of the shaft.

This exemplary measure may have the effect that via a single cable any energy and information may be transferred to and/or from the distal-side Video-/LED-unit. Given the orientation of the elongated hole opening, the flat ribbon cable applies a resistance force as low as possible when deflecting.

In a further exemplary embodiment, a series of adjacent moveable vertebral members is arranged in the deflectable section of the shaft, wherein at least the distal-side member of which is coupled with the distal end of the pull element.

The provision of the deflectable region with the vertebral members, which is a measure already known as such, may have the result that in this way sections that are deflectable in a simple and reliable fashion may be formed which also involve a sufficient mechanical stability.

Those vertebral members may be arranged in series along the longitudinal direction of the shaft and comprise respectively inclined surfaces. As it is sufficient in the context of the present disclosure, at least in some exemplary embodiments, that a deflection only in a single direction is provided, also very small vertebral members having a small diameter may be implemented which are to some extent inclined only at one side, i.e. in the direction in which the deflection shall be present. By pulling at least the most distal-side vertebral member with the pull element, the vertebral members gradually will contact and abut one another via their inclined sides and will then overall form the deflected curved section of the shaft. This further contributes to the operational safety involving a preferably slender shaft design.

In a further exemplary embodiment, at least one rebound element is arranged in the deflectable section of the shaft, wherein the at least one rebound element may generate a reset force when the deflectable section is deflected.

This measure may be applied in accordance with at least one exemplary embodiment so as to facilitate the resetting of the deflectable shaft which for instance applies to the adjacent vertebral members.

This may be for instance achieved by elastic wire-shaped bodies which extending through openings in the vertebral members. Hence, for instance respective metallic wires or wires having a memory effect, for instance Nitinol-wires, may be involved which provide for a resetting of the deflectable region. Also this may be achieved in the context of the disclosure by reliable and very slender-shaping measures in the deflectable region of the shaft.

According to a further exemplary embodiment, the endoscope comprises a single pull element that is arranged for deflecting the distal section of the shaft. It may be an option for emergency situations to provide the endoscope with the (limited) capability of deflecting in only a single lateral direction. Hence, operating the endoscope is simplified. Operation errors may be prevented. In combination with at least one rebound element, both a deflection and a return action may be achieved, even though only one pull element is provided. As a result, the occupied installation space may be further reduced.

According to a further exemplary embodiment, the push tube and the pull element are fixedly attached to a pull bolt that is coupled with the control element. In other words, in accordance with this exemplary embodiment, no relative movement between the push tube and the pull element in the main elongation direction of the pull element is present. The relative fixation between the push tube and the pull element may be achieved by jointly attaching the push tube and the pull element to the pull bolt.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and exemplary embodiments are disclosed in the description below with reference to the drawings, in which.

DETAILED DESCRIPTION OF EXEMPLARY EMBODIMENTS

An exemplary embodiment of an endoscope is shown in the Figures provided herein which is arranged as a video intubation endoscope and designated in its entirety by the reference numeral 10.

Figure 1:
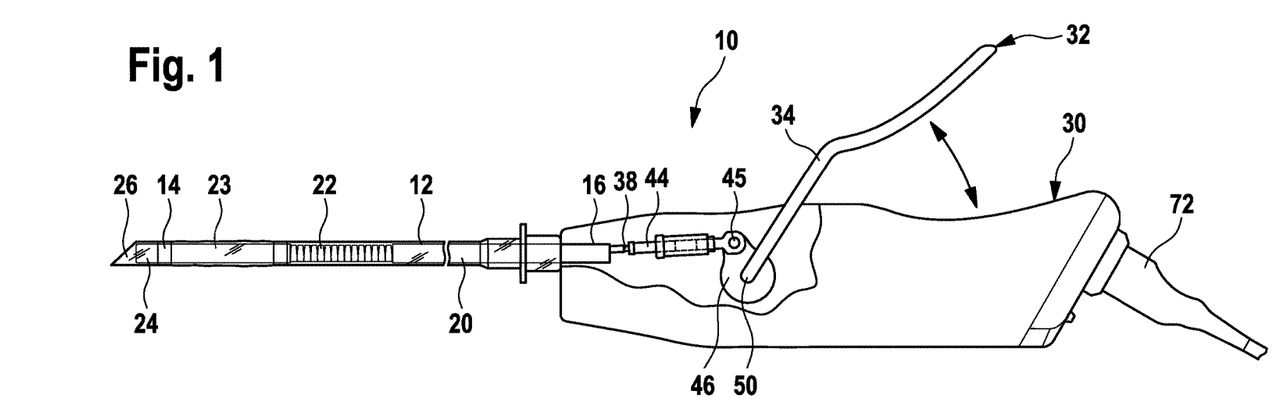
FIG. 1 shows a schematic and partially broken lateral view of an exemplary embodiment of an endoscope in a straightened state of the shaft involving an intubation tube that is pushed thereon.
Figure 2:
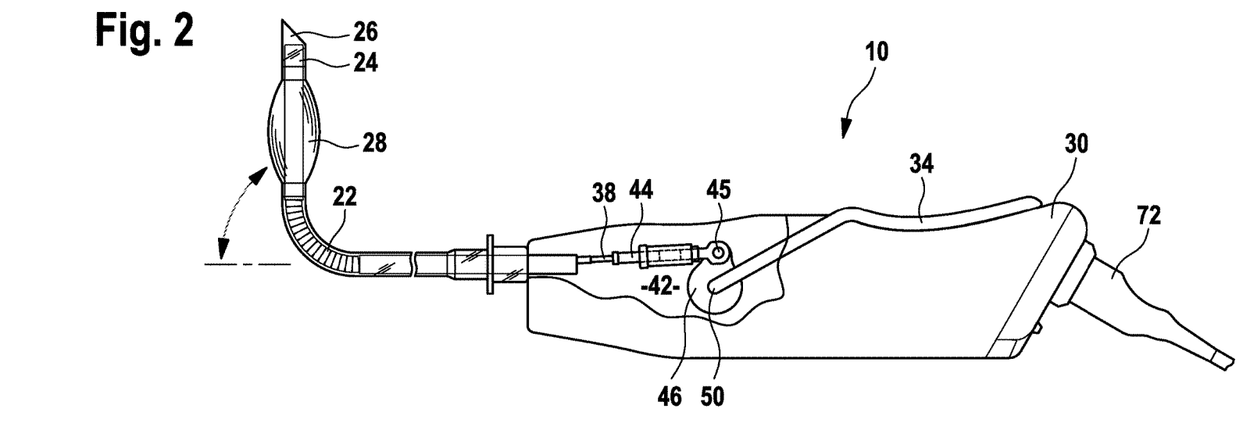
FIG. 2 is a corresponding side view, wherein the deflectable region of the shaft is deflected in a direction and wherein the intubation tube is inflated for fixation in the trachea.
Figure 3:
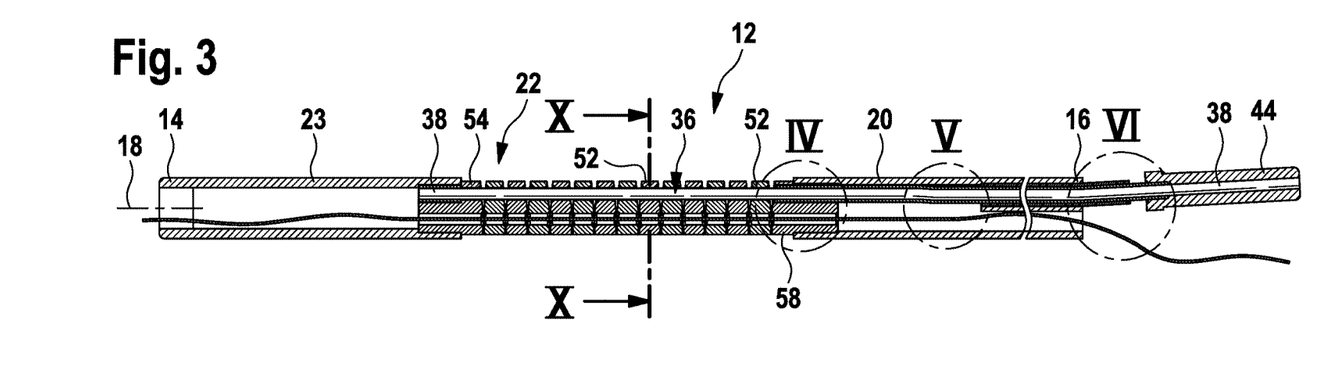
FIG. 3 is a longitudinal cross-section of an exemplary embodiment of a shaft for an endoscope as exemplarily shown in FIG. 1 and FIG. 2 in the straightened state.
Figure 4:
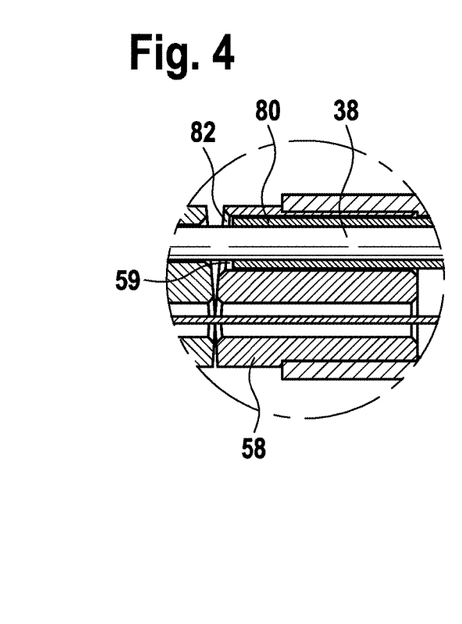
FIG. 4 is an enlarged view of the region that is delimited in FIG. 3 by a circle IV.
Figure 5:
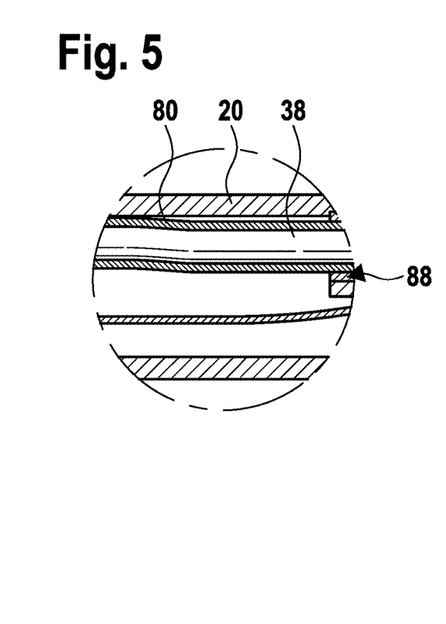
FIG. 5 is an enlarged view of the region that is delimited in FIG. 3 by a circle V.
Figures 7, 8:
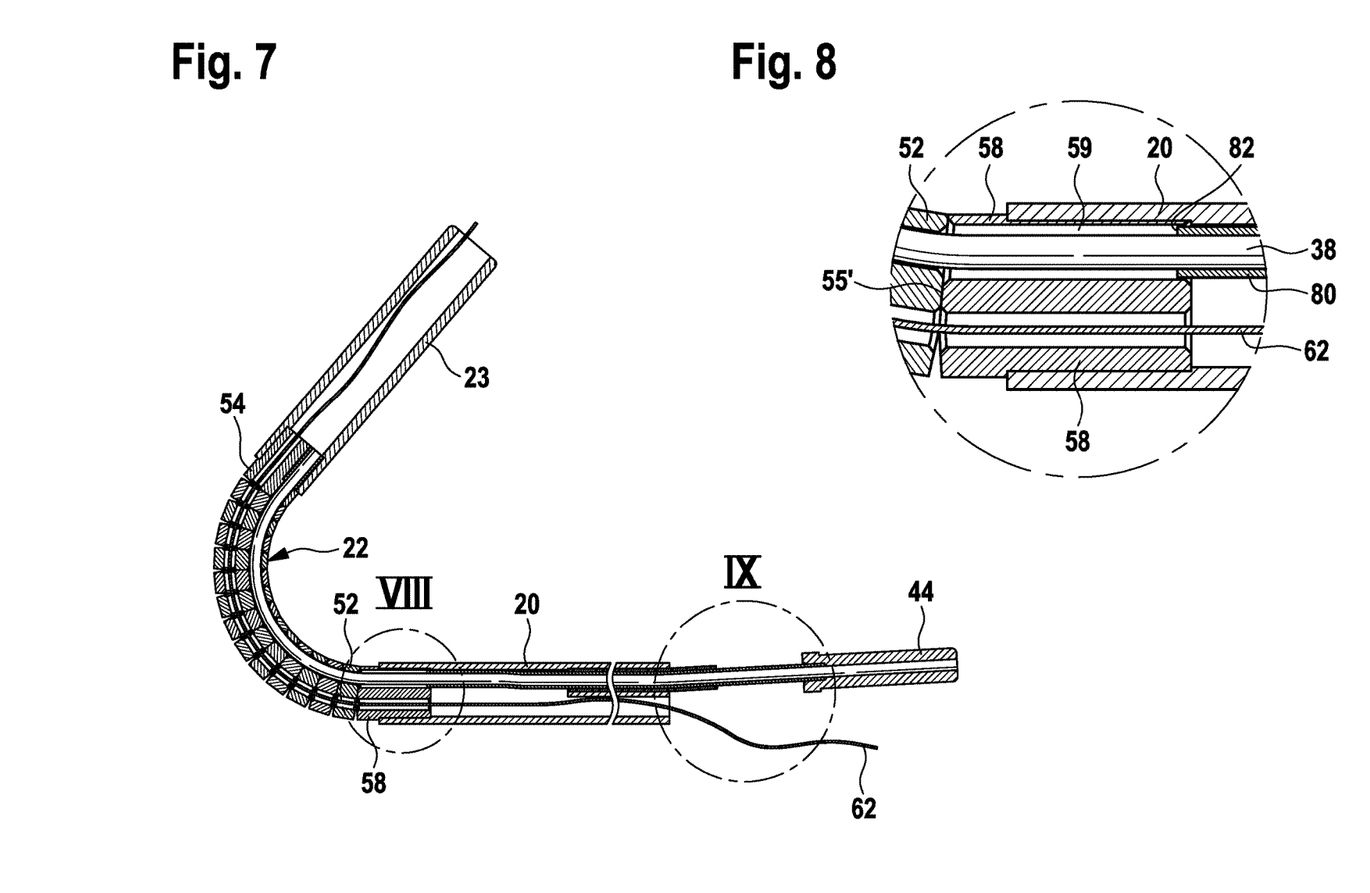
FIG. 7 a cross-sectional view of the shaft that corresponds to FIG. 3 in a laterally deflected state.
FIG. 8 an enlarged view of the region that is delimited in FIG. 7 by a circle VIII.

As can be particularly seen from FIGS. 1 and 2, the video intubation endoscope 10 comprises a shaft 12 which is shown in FIGS. 3 and 7 in isolation.

The shaft 12 comprises a distal end 14 and a proximal end 16. The shaft 12 comprises a central longitudinal axis 18 and may be moved between a linearly straightened state as shown in the FIGS. 1 and 3 and a state laterally deflected to a side as shown in FIGS. 2 and 7.

The shaft 12 comprises a rigid proximal tubular section 20, a deflectable distal section 22 distally adjoining the proximal section 20, and a rigid end 23 that is arranged in a hollow tubular fashion.

As can be particularly seen from FIG. 1 and FIG. 2, an imager/illuminator unit 24 is arranged at the distal end 14 of the shaft 12.

The unit 24 is arranged as an integrated component involving an image sensor forming an imager and at least one LED forming the illuminator. An energy supply and/or transfer of image information is performed via a supply cable 62 which is arranged as a broad ribbon cable and which extends from the distal end of the shaft through the shaft to a housing 30 which is arranged at the proximal end 16 of the shaft 12. The supply cable 62 extends through the interior of the housing 30 and is led, at the proximal end thereof via a cable sleeve 72, to respective supply sources and/or a monitor for visualizing the image.

Hence, the endoscope is arranged as a video intubation endoscope.

As shown in FIGS. 1 and 2, a flexible endotracheal tube 26 is pushed on the rigid end 23 of the shaft 12. The tube 26 is arranged to be inserted into a trachea of a patient when intubing the patient with the video intubation endoscope 10.

It may be envisaged in the field of intubation to inflate an inflatable region 28 of the tube 26 after inserting the assembly of video intubation endoscope 10 and endotracheal tube 26 at an appropriate position in the trachea so that the tube 26 is fixed in its position at the trachea. Subsequently, the video intubation endoscope 10 may be pulled off from the set tube 26. For the inflation, a syringe may be provided which is coupled with the tube 26 via a thin line so as to inflate the inflatable region 28 with air. For the sake of illustrative clarity this is not shown in more detail herein.

As can be particularly seen from FIGS. 1 and 2, the housing 30 is provided with a control element 32 that is arranged as a laterally projecting lever 34 which may be for instance arranged as a bow that is embracing the housing 30 in a U-shaped fashion. The inner housing-side end 50 of the control element 32 extends into the exterior of the housing 30 as can be seen from the broken view of FIGS. 1 and 2.

There, the control element 32 is coupled with the proximal end of a rod-like pull element 36 arranged as a pull wire 38 as will be further explained and elucidated in more detail with reference to further drawings. The pull element 36 extends through the shaft 12 and is configured for moving the deflectable section 22 of the shaft 12 from the linearly straightened orientation as shown in FIG. 1 to the laterally deflected curved orientation as shown in FIG. 2.

As can be particularly seen from FIG. 1 and FIG. 2, to this end, the proximal end region of the pull element 36 extends beyond the proximal end 16 of the shaft and into an inner clearance space 42 of the interior of the housing 30.

Therein, the pull element 36 is coupled with a pull bolt 44 which is arranged in a pivotable fashion via an axis bolt 45 at an eccentric disc 46.

Spaced from the axis bolt 45, also the inner end 50 of the afore-mentioned control element 32 is attached to the eccentric disc 46.

Hence, when the lever 34 is moved from the laterally projecting position with respect to the housing 30 as shown in FIG. 1 towards the housing which corresponds to a shift of FIG. 1 to FIG. 2, the pull bolt 44 is moved by the eccentric disc 46 in the proximal direction and, accordingly, also the pull element 36 is moved in the proximal direction into the clearance space of the housing as can be also seen from a transition from FIG. 1 to FIG. 2.

This involves a corresponding deflection of the shaft 12.

A more detailed exemplary embodiment of the shaft 12 and of further aspects and design elements thereof will be elucidated with reference to FIGS. 3 to 11. The deflectable distal section 22 is formed in the illustrated exemplary embodiment by twelve vertebral members 52 that are arranged along the central longitudinal axis 18 in a consecutive series. A more detailed design configuration of the vertebral members 52 can be seen in FIGS. 10 and 11. Those twelve vertebral members 52 are received between a distal end piece 54 and a proximal end piece 58.

This involves that the distal end piece 54 is pushed into the proximal end of the tubular end piece 23. Accordingly, the basically similarly shaped proximal end piece 58 is arranged in a mirror-symmetric fashion and pushed into the distal end of the rigid proximal section 20 of the shaft, as can be particularly seen from FIGS. 3 and 12. A through hole 53 extends through the vertebral member 52 and through the end pieces 54 and 58, wherein the hole 53 is laterally offset from the central longitudinal axis 18. The pull element 36, shaped as a thin metallic wire 38, is received in those through holes. As can be particularly seen from the illustration of FIG. 3, the distal end of the wire 38 is fixed in an immovable fashion in the distal end piece 54 via a clamping sleeve. At the proximal end, the wire 38 preferably further extends from the proximal end piece 48 through the rigid proximal section 20 of the shaft 12, exits the shaft 12 and extends into the housing 30 via a first end-side opening 40 towards the clearance space 42. Therein, the distal end of the wire 38 is coupled with the afore-mentioned pull bolt 44.

Figure 11:
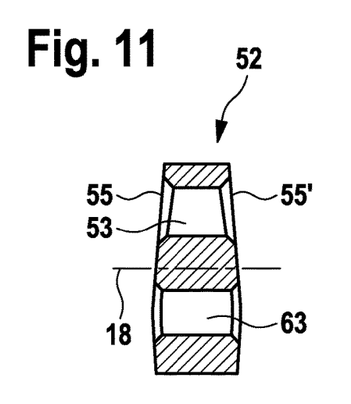
FIG. 11 a cross-sectional view along the line XI-XI in FIG. 10.

As can be particularly seen from the cross-sectional view of FIG. 11, in an exemplary embodiment, the vertebral members 52 comprise, in the region in which the hole 53 for the wire 38 extending therethrough is provided, opposite inclinations 55, 55' that are slightly inwardly directed.

Hence, when the wire 38 is pulled by means of the pull bolt 44 in the proximal direction, the respective vertebral members 52 are tilted with respect to one another until they adjoin one another via their inclinations 55, 55'. This can be particularly seen when shifting from FIG. 3 to FIG. 7. Hence, the deflected section 22 is formed.

In a final assembly state, this region is covered by an outer flexible protection cover which is not explicitly shown herein.

Figure 10:
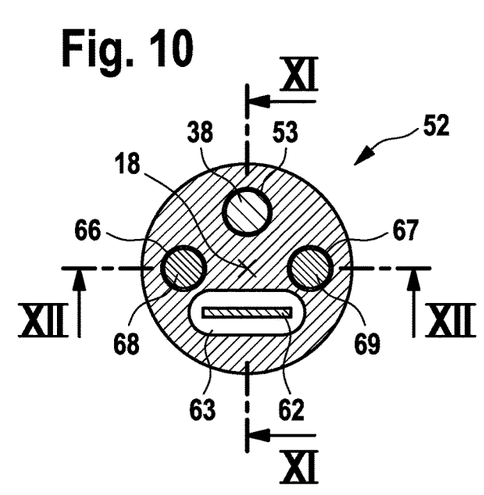
FIG. 10 a cross-section through a vertebral member along the line X-X in FIG. 3.

It can be further seen from FIGS. 10 and 11 that a further hole 63 is provided that is opposite to the hole 53, with respect to the longitudinal axis 18, and spaced away from the central longitudinal axis 18. This hole 63 is used for guiding the supply cable 62 which is arranged as a flat ribbon cable through the shaft 12. This involves that the position of the elongated hole of the elongated hole opening 63 is defined in such a way that the longer axis thereof extends transversely to the plane in which the shaft is deflectable. In this way, a continuous guide channel for the flat ribbon cable is formed in the deflectable section 22.

In the illustration of FIG. 10, a dashed line XI-XI corresponds to the deflection plane. In this direction, the flat ribbon cable 62 may be easily bent with little force exertion.

Figure 12:
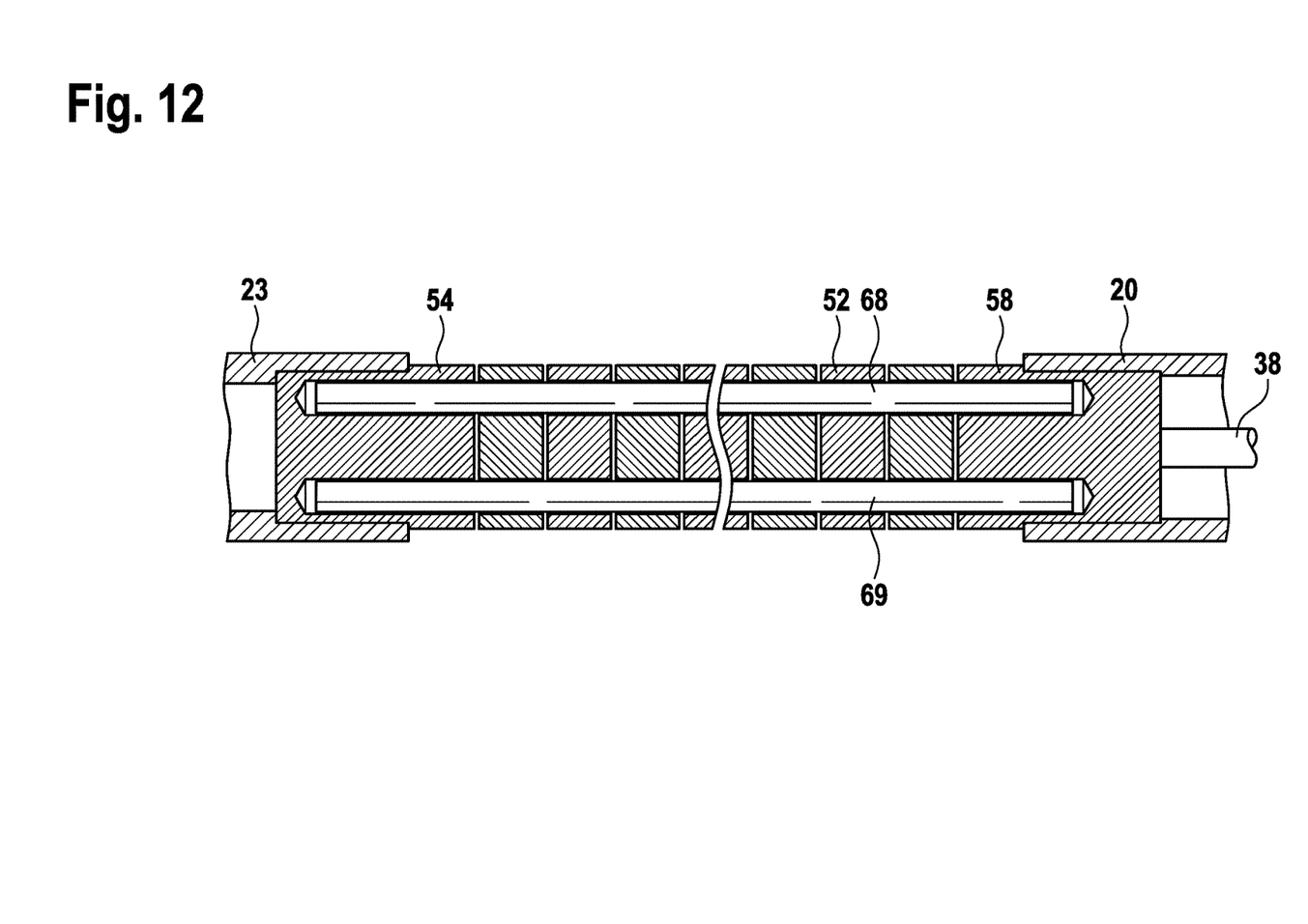
FIG. 12 a cross-sectional view along the line XII-XII in FIG. 10.

As can be deduced from FIGS. 10, 11 and 12, further holes 66 and 67 are provided in the vertebral members 52 which end in the end pieces 54 and 58 as blind hole holes.

Those holes 66 and 67 are configured for receiving wire-like and/or rod-like rebound elements 68 and 69 which are formed in the exemplary embodiment from Nitinol-wires.

Those rebound elements 68 and 69 are bent when transforming from the configuration of FIG. 1 to FIG. 2, and this involves a formation of a reset force. Hence, when the lever 34 is released in the position shown in FIG. 2, the reset force of the rebound elements 68, 69 ensures that the shaft returns into the linearly orientated position shown in FIG. 1.

The detailed structure of the proximal end region of the shaft 12 is illustrated in the cross-sectional views of FIGS. 3 to 6.

Figure 6:
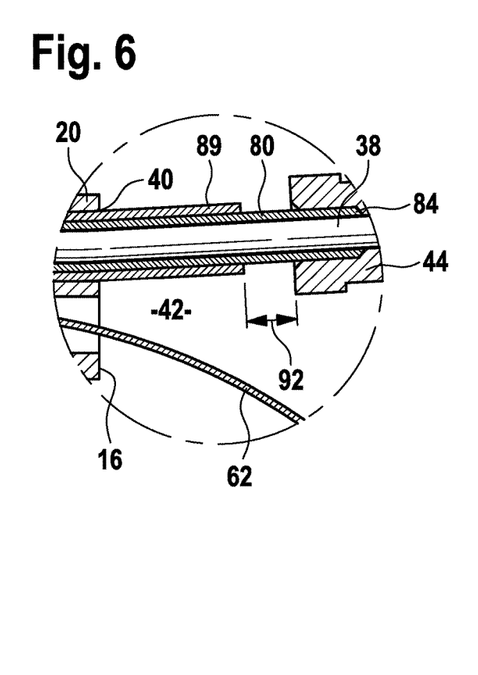
FIG. 6 is an enlarged view of the region that is delimited in FIG. 3 by a circle VI.

It can be seen from FIGS. 3 and 6 that at the proximal end 16 of the shaft 12, a first opening 40 is provided in which a guide 88 arranged as a guide tube 89 is inserted. The guide 88 extends, at the distal side, along a certain longitudinal section into the interior of the rigid proximal section 20 as can be particularly seen from FIGS. 3 and 5.

It can be seen from FIG. 6 that the guide tube 89 also extends at the proximal side away from the proximal end 16 of the shaft 12 and into the clearance space 42. The length of the extension into the clearance space 42 is selected in such a way that in the straightened orientation of the shaft 12 illustrated in FIG. 3 and FIG. 6 only a relatively small distance 92 is present between the proximal end of the guide tube 89 and the distal end of the pull bolt 44 that is opposite thereto.

It can be further seen from FIGS. 3 to 9 that a push tube 80 is pushed on and/or encased around the exterior side 39 of the wire 38. That is, the inner side of the push tube 80 adjoins the exterior side 39 of the wire. The push tube 80 is made from a metallic tube sleeve from stainless steel.

As can be particularly seen from the view of FIG. 6, the proximal end 84 of the push tube 80 is attached to a corresponding hole at the pull bolt 44 in an immovable fashion. In other words, in this region both the push tube 80 and also the wire 38 are attached to the pull bolt 44 in a fixed fashion and in a manner not displaceable with respect to one another.

The push tube 80 extends at the proximal side through the guide tube 89 and the guide 88 so far into the interior of the rigid proximal section 20 of the shaft 12 that it also extends into the proximal end piece 58 and is guided therein. This can be particularly seen from FIG. 4, i.e. in the linearly straightened state of the shaft, the distal end 82 of the push tube 80 ends approximately at the level of the distal end of the proximal end piece 58. Distal-sided of this position, only the pull element 36 extends through the vertebral members 52, but not the push tube 80.

Figure 9:
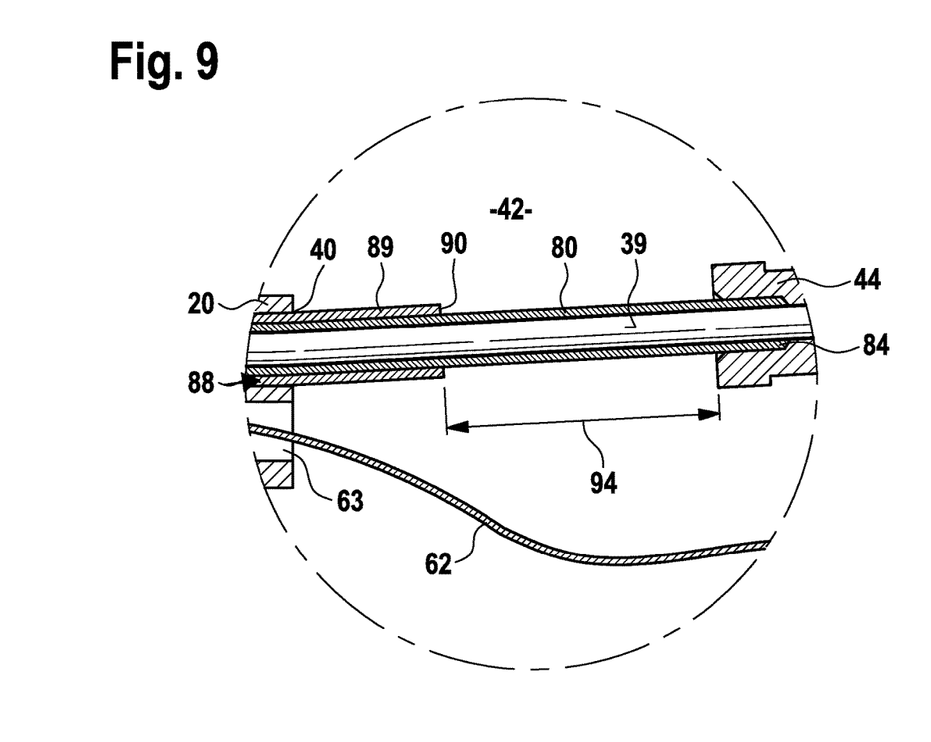
FIG. 9 an enlarged view of a region that is delimited in FIG. 7 by a circle IX.

When the shaft 12 is curved as is shown in FIG. 2 and in FIG. 7, the pull bolt 44 is moved in the proximal direction and the assembly of push tube 80 and wire 38 is moved in the proximal direction. In FIG. 9, the maximum displacement is shown. It can be deduced therefrom that now the distance 94 between the proximal end 90 of the guide tube 89 and the frontal end of the pull bolt 44 that is arranged opposite thereto is considerably larger than the distance 92 shown in FIG. 6. The frontal end of the pull bolt 44 also may be referred to as distal end.

In this region, the wire 38 would be basically exposed if it was not protected, particularly strengthened, by the push tube 80 in accordance with at least some exemplary aspects and embodiments of the present disclosure. Due to the push tube which particularly extends into this critical distance region 94, it is ensured that no bulges or lateral evasion of the wire 38 may occur in this region when the pull bolt 44 is moved from the position illustrated in FIG. 9 to the position illustrated in FIG. 6. It can be derived from FIG. 8 that in the state shown in FIG. 9, the distal end 82 of the push tube 80 is also moved in the guide 88 in the interior of the shaft 12 in the proximal direction but is still received in that guide 88 and in the end piece 58.

In this way, the displacement movements of the pull element 36, when bending the shaft and particularly when subsequently linearly aligning the shaft, may be guided and accomplished in a safe and particularly reliable fashion.

What is claimed is:

1. A video endoscope, comprising:
 a shaft comprising:
  a rigid, proximal-side section, and
  a deflectable section at a distal end of the shaft, that is laterally deflectable from a central longitudinal axis of the shaft,
 an imager and an illuminator that are arranged at a distal end of the deflectable section, a pull element arranged in the shaft in an off-center fashion with respect to the central longitudinal axis,
a housing that is arranged at a proximal end of the shaft,
a control element arranged at the housing for controlling the deflection of the shaft, and
a push tube that encases an exterior side of the pull element,
wherein the pull element is, at a proximal side thereof, coupled with the control element and, at a distal side thereof, coupled with the distal end of the deflectable section of the shaft in such a way that a movement of the pull element in the proximal direction that is induced by the control element effects a lateral deflection of the deflectable section,
wherein the cod like pull element extends into a clearance space of the housing through a first opening at the proximal end of the shaft,
wherein a proximal end of the pull element is coupled with the control element in the clearance space, forming a proximal connection,
wherein the push tube extends from the proximal connection of the pull element with the control element through the first opening and into the shaft, when the shaft is straightened, and
wherein the push tube is arranged to fully cover a region of the pull element that is arranged in the clearance space of the housing when the pull element is maximally displaced in the proximal direction.

2. The video endoscope as claimed in claim 1, wherein a proximal end of the push tube and the pull element are jointly coupled with the control element in a fashion non-displaceable with respect to one another.

3. The video endoscope as claimed in claim 1, wherein, seen from proximal to distal, a distal end of the push tube ends, when the shaft is straightened, in a fashion offset in the proximal direction from a proximal end of the deflectable section of the shaft.

4. The video endoscope as claimed in claim 1, wherein the push tube extends through the first opening into the shaft when the pull element is maximally displaced in the proximal direction.

5. The video endoscope as claimed in claim 1, further comprising a guide in the rigid proximal section of the shaft, wherein the push tube is guided in the guide.

6. The video endoscope as claimed in claim 5, wherein the guide comprises a guide tube that extends from a proximal end of the first opening into the clearance space, and wherein an assembly formed by the push tube and the pull element extends through the guide tube.

7. The video endoscope as claimed in claim 6, wherein the length of the guide tube that extends into the clearance space is defined in such a way that, when the shaft is straightened, the assembly formed by the pull element and the push tube between the first opening and the connection with the control element is covered by the guide tube.

8. The video endoscope as claimed in claim 1, wherein the push tube is made from metal material.

9. The video endoscope as claimed in claim 1, wherein a supply cable is provided that extends through the shaft, wherein the supply cable is, at a distal side thereof, coupled with a unit formed by the imager and the illuminator, and wherein the supply cable extends through a second opening at the proximal end of the shaft into the clearance space.

10. The video endoscope as claimed in claim 9, wherein the supply cable is a flat ribbon cable, and wherein a guide channel for the flat ribbon cable is provided in the deflectable section, the guide channel forming, in cross-section, an elongated hole opening having a major axis and a minor axis, wherein the major axis extends transversely to a swivel plane of the deflectable section of the shaft.

11. The video endoscope as claimed in claim 1, wherein a series of moveable vertebral members that are arranged adjacent to one another is provided in the deflectable section of the shaft, and wherein at least a distal-side member of the series is coupled with a distal end of the pull element.

12. The video endoscope as claimed in claim 1, wherein at least one rebound element is arranged in the deflectable section of the shaft, and wherein the at least one rebound element is arranged to generate a reset force that acts on the shaft, when the deflectable section is deflected.

13. The video endoscope as claimed in claim 1, wherein at least one rebound element is arranged in the deflectable section of the shaft that is arranged for transferring the deflectable section from a deflected state to a non-deflected state so that the shaft is straightened, and wherein the pull element is arranged for transferring the deflectable section from the non-deflected state to the non-deflected state when the control element is operated to pull the pull element.

14. The video endoscope as claimed in claim 1, further comprising a pull bolt that is operatively coupled with the control element, wherein the push tube and the pull element are fixedly attached to the pull bolt in a manner non-displaceable with respect to one another.

15. The video endoscope as claimed in claim 1, wherein the video endoscope is arranged as a video intubation endoscope.

16. A video endoscope, comprising
a shaft comprising
a rigid, proximal-side section, and
a deflectable section at a distal end of the shaft that is laterally deflectable from a central longitudinal axis of the shaft,
a pull element arranged in the shaft in an off-center fashion with respect to the central longitudinal axis,
a housing that is arranged at a proximal end of the shaft,
a control element arranged at the housing for controlling the deflection of the shaft, and
a protective push tube that encases an exterior side of the pull element,
wherein the pull element is, at a proximal side thereof, coupled with the control element and, at a distal side thereof, coupled with a distal end of the deflectable section of the shaft,
wherein the control element is movably supported by the housing,
wherein the control element is operable between a first state and a second state,
wherein the deflectable section is straightened when the control element is in the first state,
wherein the deflectable section is deflected when the control element is in the second state,
wherein the pull element is displaced in the proximal direction when the control element is in the second state,
wherein a proximal end of the pull element is coupled with the control element in a clearance space of the housing, forming a proximal connection,
wherein the push tube extends from the proximal connection of the pull element with the control element through the clearance space of the housing into the shaft, when the shaft is straightened, and
wherein the push tube is arranged to cover a region of the pull element that is arranged in the clearance space of the interior of the housing when the pull element is maximally displaced in the proximal direction.

17. The video endoscope as claimed in claim 16, wherein the pull element is movable between a first, extracted position and a second, retracted position, wherein the push tube is arranged to cover the region of the pull element that is arranged in the clearance space in the first position of the pull element and in the second position of the pull element.

18. A video endoscope, comprising
a shaft comprising
a rigid, proximal-side section, and
a deflectable section at a distal end of the shaft that is laterally deflectable from a central longitudinal axis of the shaft,
an imaging and illumination unit arranged at a distal end of the deflectable section,
a pull element arranged in the shaft in an off-center fashion with respect to the central longitudinal axis,
a housing that is arranged at a proximal end of the shaft,
a control element arranged at the housing for controlling the deflection of the shaft, and
a push tube that encases an exterior side of the pull element,
wherein the pull element is, at a proximal side thereof, coupled with the control element and, at a distal side thereof, coupled with the distal end of the deflectable section of the shaft,
wherein a movement of the pull element in the proximal direction that is induced by an actuation of the control element effects a lateral deflection of the deflectable section,
wherein the rod like pull element extends into a clearance space of the housing,
wherein a proximal end of the pull element is coupled with the control element in the clearance space,
wherein the push tube extends between the proximal end of the pull element and the shaft and extends through a first opening at the proximal end of the shaft,
wherein the push tube and the pull element are jointly moved in a fashion non-displaceable with respect to one another when the control element is actuated, and
wherein the push tube covers a region of the pull element that is arranged in the clearance space when the pull element is maximally displaced in the proximal direction
wherein a rebound rod is arranged in the deflectable section of the shaft that is arranged for transferring the deflectable section from a deflected state to a non-deflected state so that the shaft is straightened, and
wherein the pull element is arranged for transferring the deflectable section from the non-deflected state to the non-deflected state when the control element is actuated to pull the pull element in the proximal direction.

19. The video endoscope of claim 1, wherein the control element has a control lever connected to a cam, and a push bolt, wherein the push bolt is connected to the pull element.

20. The video endoscope of claim 16, wherein the control element has a control lever connected to a cam, and a push bolt, wherein the push bolt is connected to the pull element.

* * * * *

UNITED STATES PATENT AND TRADEMARK OFFICE
CERTIFICATE OF CORRECTION

PATENT NO. : 10,285,580 B2
APPLICATION NO. : 15/142081
DATED : May 14, 2019
INVENTOR(S) : Ansgar Brambrink et al.

It is certified that error appears in the above-identified patent and that said Letters Patent is hereby corrected as shown below:

On the Title Page

Column 1, (71) Applicants:
"Karl Storz SE & Co. KG, Tuttlingen (DE); Oregon Health & Sciende University, Portland, OR (US)"

Should read:
--Karl Storz SE & Co. KG, Tuttlingen (DE); Oregon Health & Science University, Portland, OR (US)--

Signed and Sealed this
Twenty-second Day of October, 2019

Andrei Iancu
*Director of the United States Patent and Trademark Office*